(12) United States Patent
Slamani et al.

(10) Patent No.: US 7,502,693 B1
(45) Date of Patent: Mar. 10, 2009

(54) SPECTRAL FEATURE-BASED IDENTIFICATION OF SUBSTANCES

(75) Inventors: Mohamed-Adel Slamani, Alexandria, VA (US); Thomas H. Chyba, Tijeras, NM (US); Ryan E. Da Re, Bristow, VA (US); James E. Pendell Jones, Baltimore, MD (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 11/862,803

(22) Filed: Sep. 27, 2007

(51) Int. Cl.
*G06F 17/00* (2006.01)
*G01N 21/00* (2006.01)

(52) U.S. Cl. .................. 702/23; 702/22; 702/30; 702/32; 250/339.12; 250/340

(58) Field of Classification Search .............. 702/23, 702/22, 30, 32
See application file for complete search history.

(56) References Cited

U.S. PATENT DOCUMENTS

| | | | |
|---|---|---|---|
| 6,788,407 B1 | 9/2004 | Higdon et al. | |
| 6,834,122 B2 | 12/2004 | Yang et al. | |
| 6,847,446 B2 | 1/2005 | Shilling | |
| 6,922,645 B2 * | 7/2005 | Haaland et al. | 702/76 |
| 6,949,734 B2 | 9/2005 | Neff et al. | |
| 7,009,170 B2 | 3/2006 | Dobbs et al. | |
| 7,099,003 B2 | 8/2006 | Saptari et al. | |
| 7,127,372 B2 | 10/2006 | Boysworth | |
| 7,333,190 B1 * | 2/2008 | Pendell-Jones et al. | 356/73 |
| 7,359,040 B1 * | 4/2008 | Pendell-Jones et al. | 356/73 |
| 2001/0052978 A1 * | 12/2001 | Lewis et al. | 356/326 |
| 2002/0031843 A1 | 3/2002 | Harmon | |

* cited by examiner

*Primary Examiner*—Hal D Wachsman
(74) *Attorney, Agent, or Firm*—Edell, Shapiro & Finnan, LLC

(57) ABSTRACT

A spectroscopic identification method and system are provided that uses the primary or main spectroscopic features of a source, such as those as arising from chemical functional groups, to describe and distinguish the source. These primary spectroscopic features make up a portion (i.e., are a subset) of the entire spectroscopic data for a particular source but can nevertheless be used as the basis of separating spectra from multiple source. When analyzing spectroscopic data obtained from a sample for one or more sources, the analysis first focuses on the primary spectroscopic features for a source rather than the entire spectra for a source.

14 Claims, 6 Drawing Sheets

SPECTRAL FEATURE-BASED IDENTIFICATION OF SUBSTANCES

BACKGROUND OF THE INVENTION

The present invention is directed to spectroscopic analysis and more particularly to a technique to improve the accuracy of spectroscopic analysis.

Spectroscopy is a well known technique to analyze the spectral properties associated with a source, such as a substance or object/scene being imaged, in order to identify compounds in the substance or particular objects in the scene. For example, spectroscopic techniques are used in Raman scattering techniques whereby a sample is illuminated with light and the spectrum of the scattered energy from the substance is analyzed to identify a specific substance as being present in the sample. High correlation between spectra of different substances, spectral clutter, and noise limit the sensitivity (i.e., decrease the probability of correct detection and identification) and specificity (i.e., increase false alarm rate) for many currently available spectroscopic techniques.

What is needed is a spectroscopic detection technique and system that is more accurate than techniques heretofore known.

SUMMARY OF THE INVENTION

Briefly, the present invention is directed a spectroscopic featured-based detection or identification system and method. The present invention uses the primary or main spectroscopic features of a source, such as those as arising from chemical functional groups, to describe and distinguish the source. These primary spectroscopic features make up a portion (i.e., are a subset) of the entire spectroscopic data for a particular source but can nevertheless be used as the basis of separating spectra from multiple sources. Thus, when analyzing spectroscopic data obtained from a sample for one or more sources, the analysis first focuses on the primary spectroscopic features for a source rather than the entire spectra for a source. This techniques reduces the correlation between sources of interest and other sources and makes it easier for an identifier to achieve optimum performance (i.e., reduced false alarms and maximum detections).

Thus, according to the present invention a method is provided for analyzing spectroscopic data to separate spectral data for at least one source from the spectroscopic data. The primary spectral features of the spectroscopic data for one or more sources of interest are identified and data is stored for the primary spectral features of the at least one source. Then, spectroscopic data is obtained from a sample and is first analyzed with the stored data for the primary spectral features to eliminate from consideration a source whose primary spectral features are not present in the spectroscopic data for the sample. The spectroscopic data for the sample is further analyzed using knowledge of one or more sources that are eliminated by the first analysis, in order to identify one or more sources present in the sample. The source may be a substance of interest, such as a chemical or biological agent, or may be a particular object of interest in an imaged scene.

DETAILED DESCRIPTION

The present invention is directed to improving the accuracy of spectroscopic analysis techniques, such as used in techniques for spectroscopic-based substance detection or spectroscopic-based imagery by introducing an analysis step that eliminates sources whose primary or main spectral features are not present in the sample spectroscopic data. Thus, the term source is used herein to include, without limitation a substance that has a spectral signature, as well as an object that has a spectral signature when a spectral imagery is employed. Examples of substances are chemical, biological or other compounds, in solid, liquid or gas form. For example, a substance of interest may be an agent of chemical and/or biological makeup that is harmful to humans, and thus whose presence is desired to be detected. Examples of objects of interest are military vehicles hidden under trees detected through sub-pixel processing of their spectral data to identify the presence of material the vehicles are made of.

Figure 1:
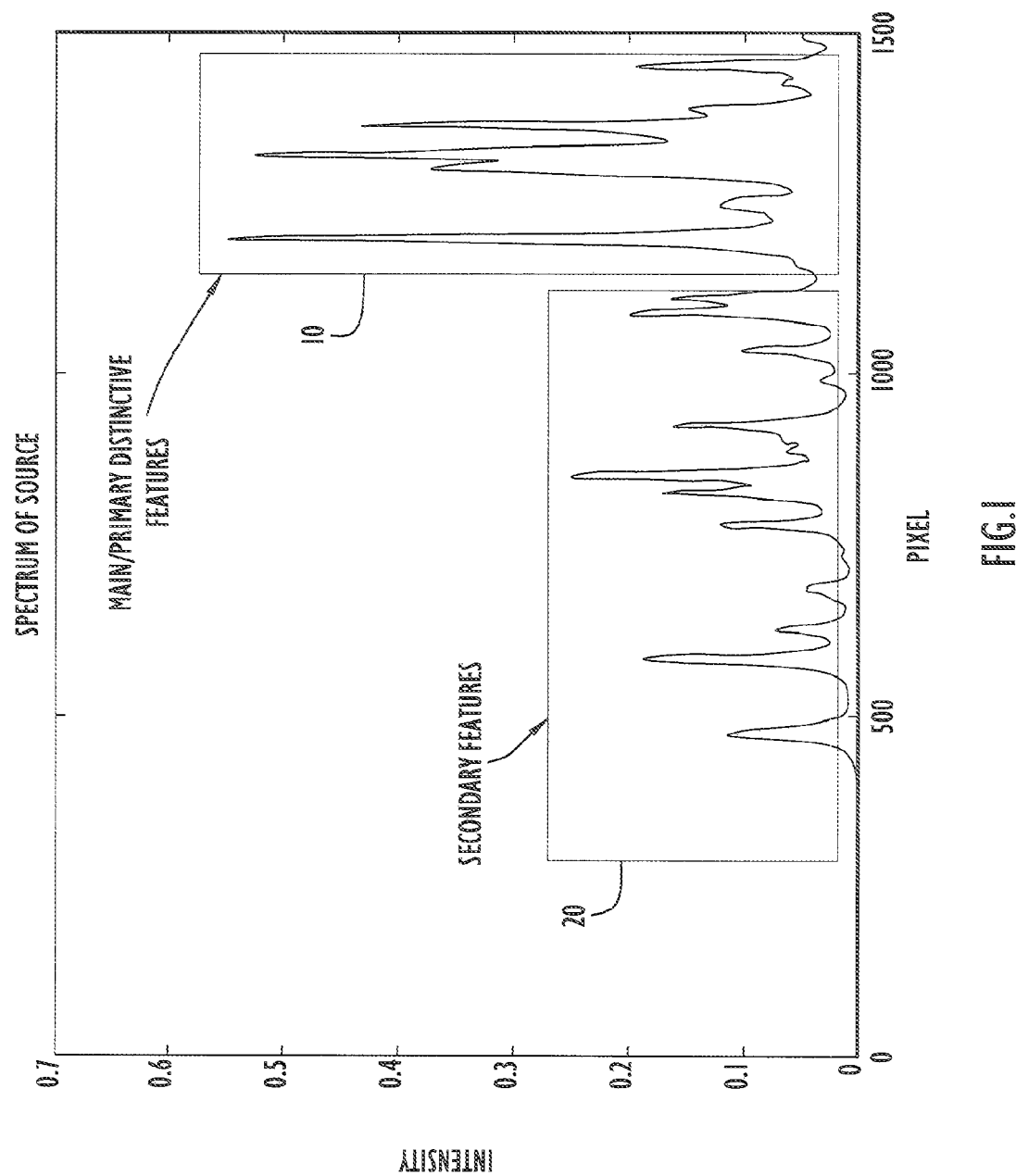
FIG. 1 is a diagram showing primary and secondary spectral features associated with a source according to an embodiment of the present invention.

Referring first to FIG. 1, a plot of the spectrum (also called spectroscopic data) associated with a particular source is shown. The spectrum is obtained using any conventional spectroscopy apparatus or system. FIG. 1 shows that the plot of the spectrum for the source has different characteristics or shapes. For example, at the higher pixels (wavenumbers), there are three relatively sharp and strong spikes. The portion of the spectrum for this exemplary source that contains these three spikes may be designated the main or primary (distinctive) spectral features at reference numeral 10 for this particular source. By contrast, the portions of the spectrum for this agent that reside at lower wavenumbers (or pixels) may be designated the secondary spectral features at reference numeral 20 because they do not distinguish the source from the spectrum of other sources as well as the primary spectral features. Thus, as shown in FIG. 1, the spectroscopic data corresponding to the primary spectral features for a source are a subset of the entire spectroscopic data for the source.

Figure 2:
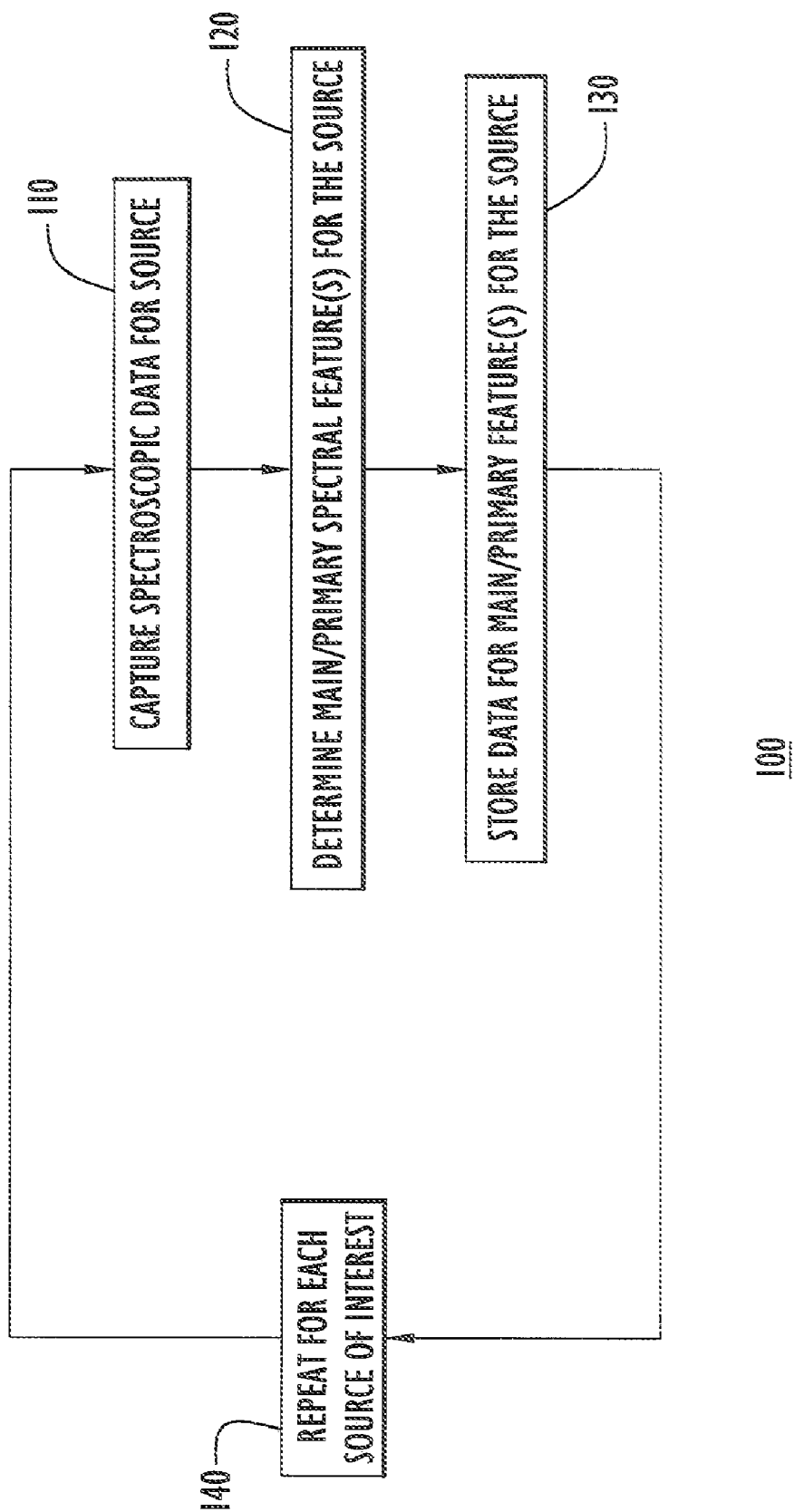
FIG. 2 is a flow chart illustrating a primary spectral feature determination process according to an embodiment of the present invention.
Figure 3:
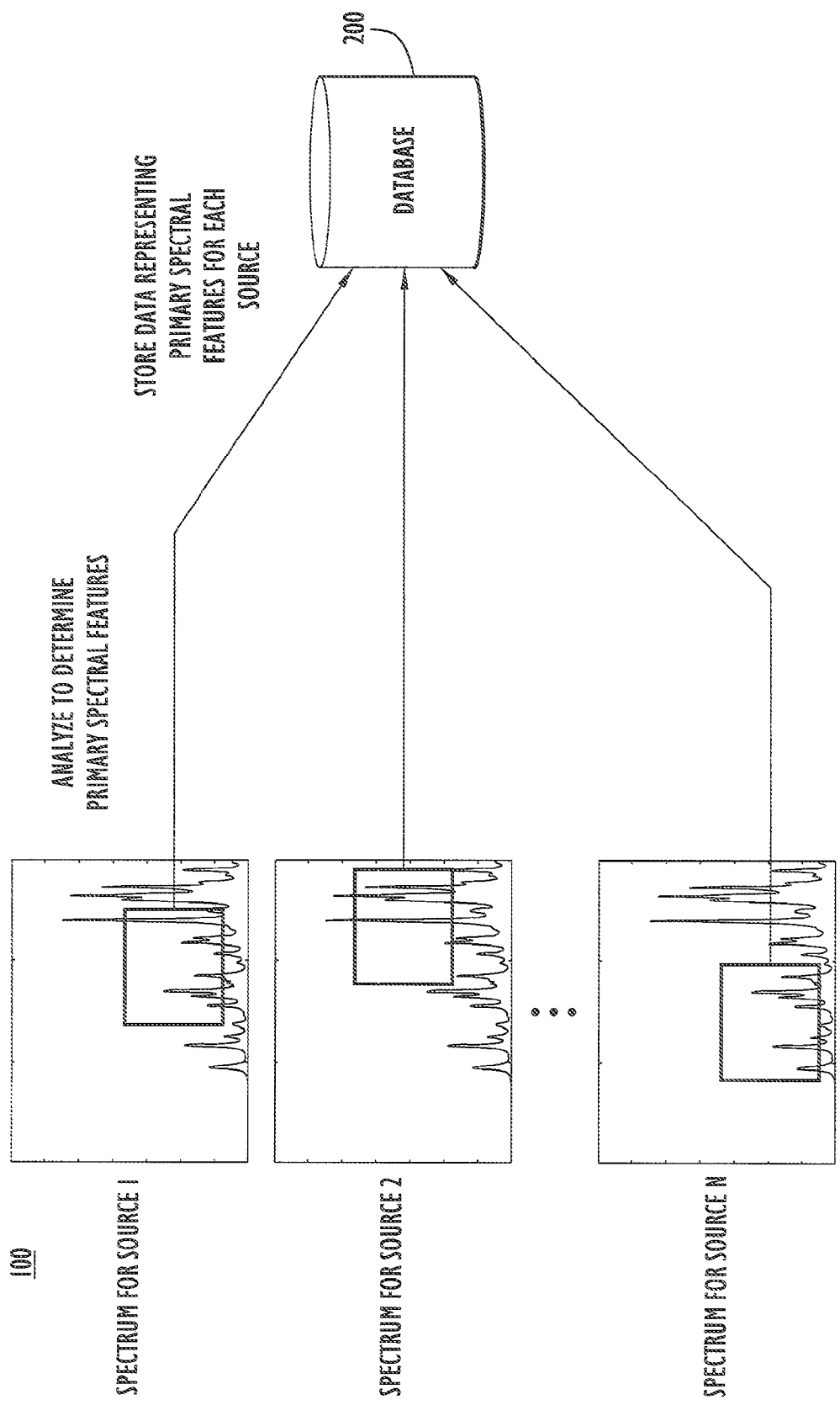
FIG. 3 is a diagram pictorially representing the feature determination process shown in FIG. 2.

Turning to FIGS. 2 and 3, a spectral feature determination process according to an embodiment of the present invention is described. The spectral feature determination process, shown at 100, involves analyzing the spectroscopic data for a source to determine or identify the one or more features of the spectral data for the source that distinguish it from other sources. For example, in the case where the source is a substance, it is known that there are spectroscopic features of a substance that arise from the constituent chemical functional groups of the substance. These features, once identified or determined, may be used to simplify and improve the accuracy of spectroscopic basis identification techniques. Specifically, by focusing on the primary spectral features for a source rather than entire spectra for the source reduces the correlation between sources of interest and other sources and makes the process more accurate by reducing false detections.

Thus, in the spectral feature determination process 100, the spectroscopic data for a source of interest is captured at 110

(e.g., from stored spectroscopic data for that source), where the spectroscopic data may have been obtained in a laboratory or field environment at some prior point in time. At 120, the spectroscopic data for the source is analyzed to determine its main or primary spectral features. This may involve examining the shapes, location of spikes, height of spikes, etc., as compared with the spectral data for other sources. Features are determined through means such as correlation analysis (in order to determine the most prominent features for a given agent) or functional group analysis which consists of inspecting the primary chemical bonds between atoms forming a molecule. At 130, data is stored to represent the primary spectral features determined at 120, such as in a database shown at reference numeral 200 shown in FIG. 3. As shown at 140, this process is repeated from each of a plurality of sources of interest.

Figure 4:
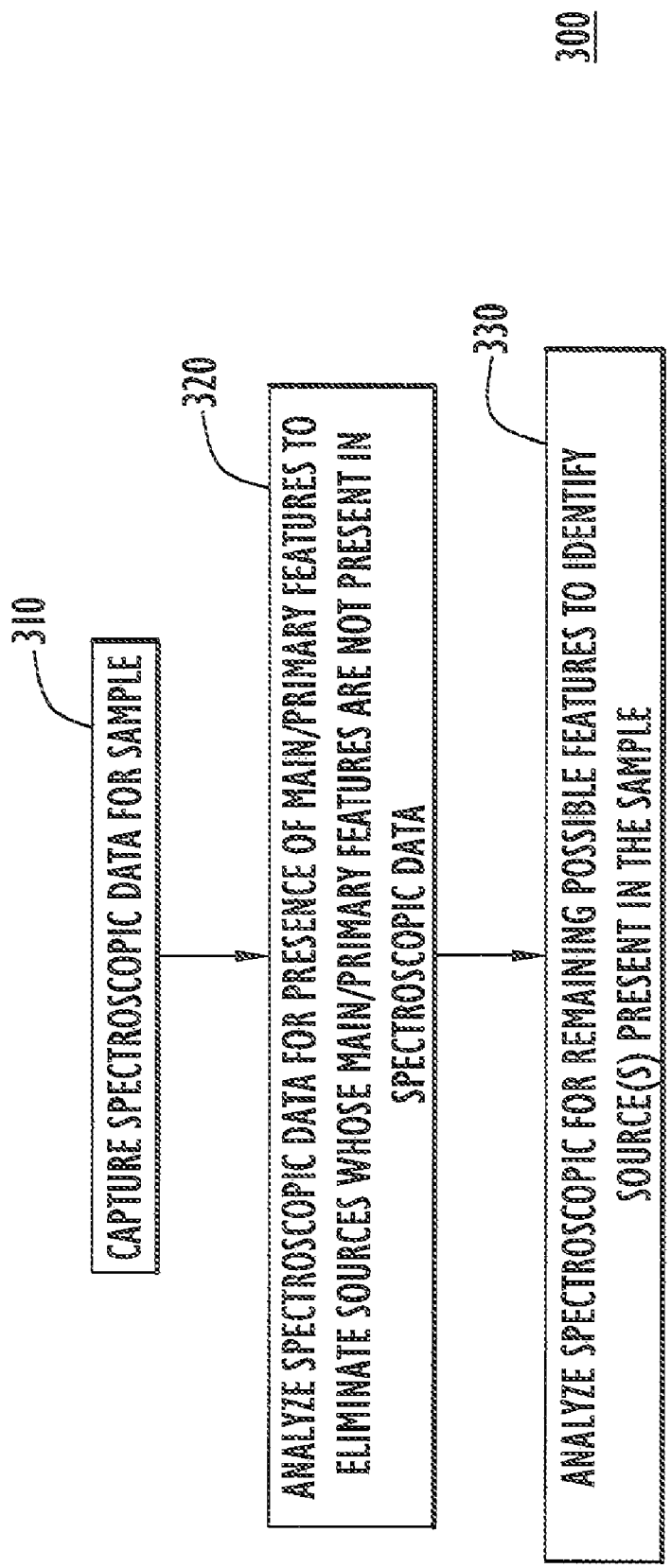
FIG. 4 is a flow chart illustrating a spectral feature-based identification algorithm according to an embodiment of the present invention using data collected from the spectral feature determination process depicted in FIGS. 2 and 3.
Figure 5:
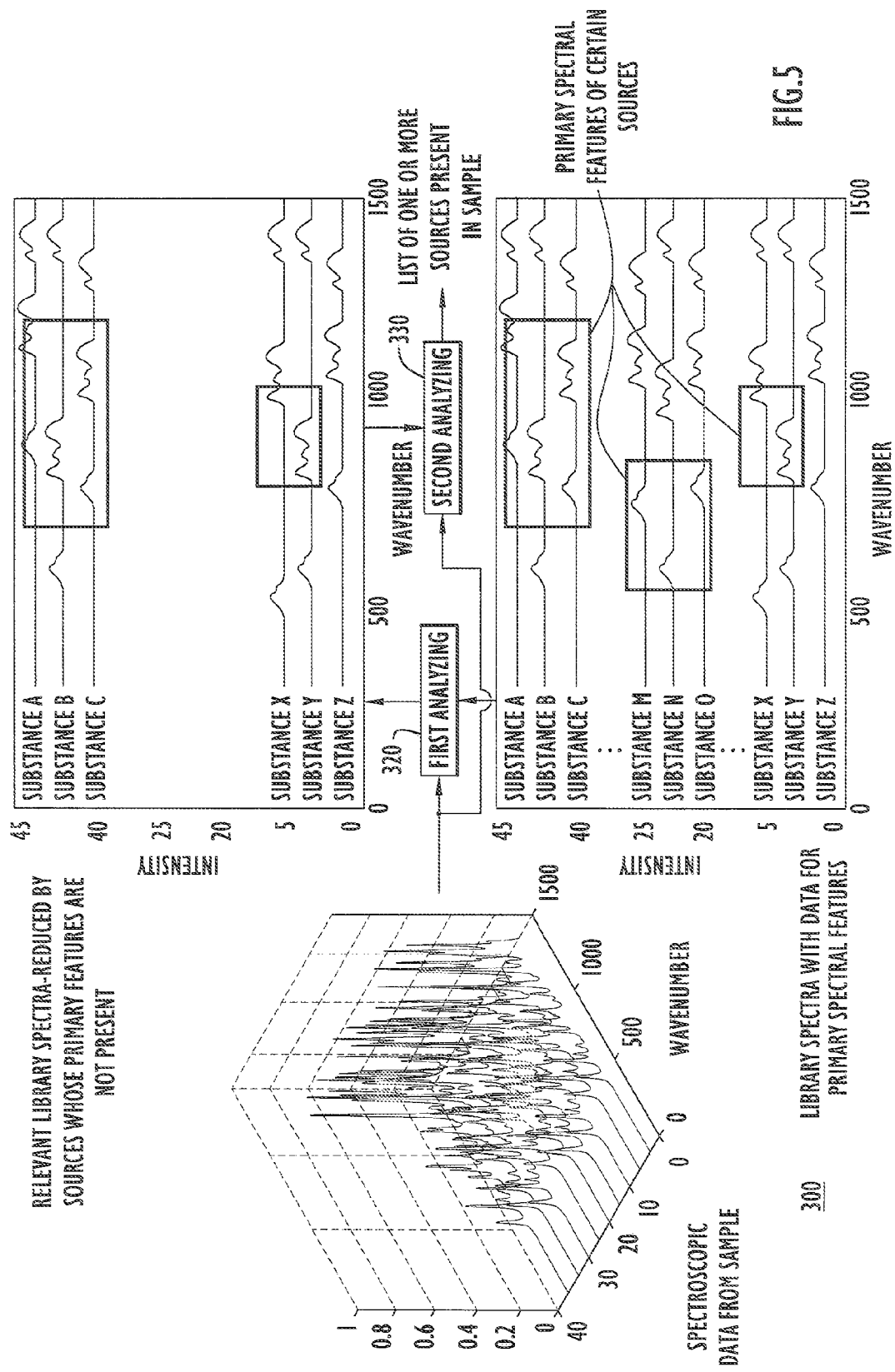
FIG. 5 is a diagram pictorially representing the spectral feature-based identification algorithm shown in FIG. 4.

Turning to FIGS. 4 and 5, a spectroscopic feature-based identification process shown at reference numeral 300 is now described. The process 300 uses the spectral feature data determined in process 200 for one or more substances of interest. At 310, the spectroscopic data is captured for a sample to be analyzed. The sample may consist of a solid, liquid or gas substance, including airborne substances as well as substance on surfaces, or a scene that is imaged using spectral imagery techniques. As 320, the spectroscopic data for the sample is analyzed against the library spectra for the presence of the primary spectral features. FIG. 5 shows the boxes for portions of the library spectra that correspond to the primary spectral features for exemplary sources contained in the library spectra. FIG. 5 also shows how the relevant library spectra can be reduced or simplified by eliminating from further consideration the sources whose primary features are not present in the sample spectroscopic data. Thus, the first analysis performed at 320 eliminates the library spectra for the one or more sources whose primary spectral features are not present in the spectroscopic data.

At 330, a second analysis is performed of the spectroscopic data for the remaining possible features, thereby more closely analyzing the spectroscopic data against the reduced library spectra. FIG. 5 shows the reduced library spectra where some of the sources are eliminated because their primary features were determined at 320 not to be present in the sample spectroscopic data. Thus, the second analysis allows for detecting the presence of one more sources that were not eliminated based on the primary spectral feature analysis at 320. Thus, the identify of sources in the sample can be determined with greater accuracy.

Figure 6:
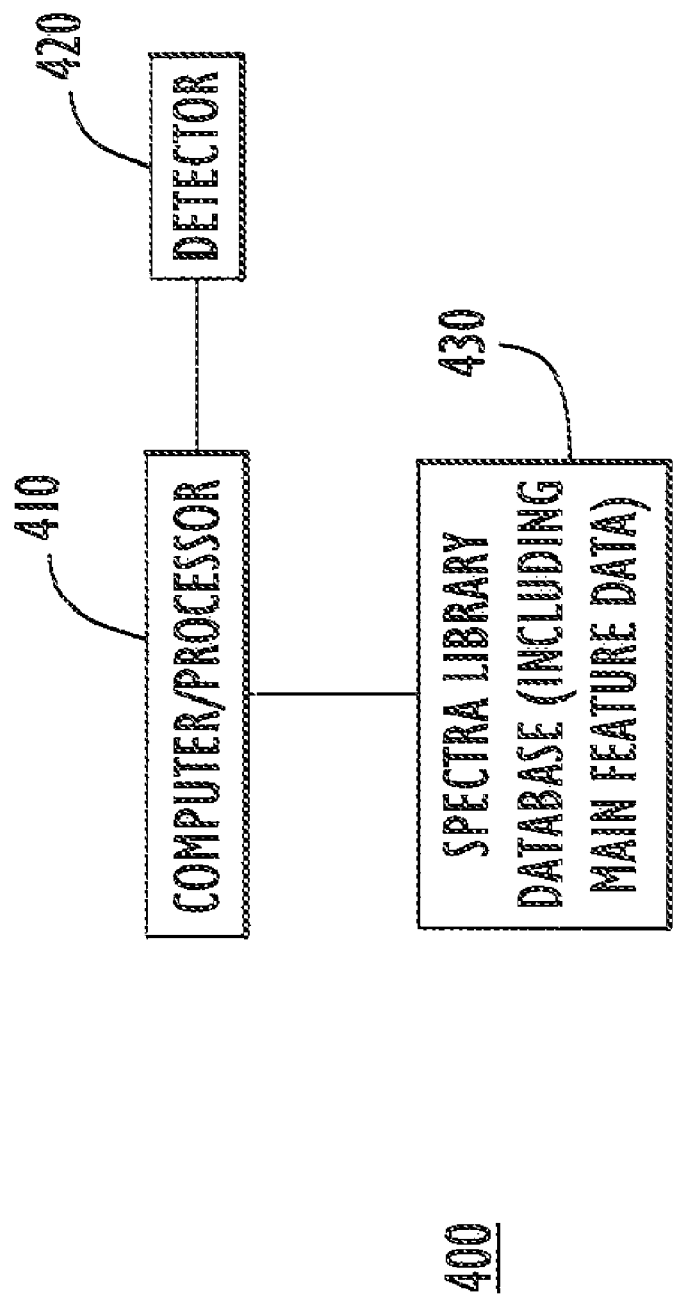
FIG. 6 is a block diagram of a spectral feature-based identification system according to an embodiment of the present invention.

FIG. 6 illustrates a block diagram of a spectroscopic detection system 400. The system 400 comprises a computer or processor 410, a spectroscopic detector 420 and a database 430 containing library spectra data including the primary spectral feature data obtained by the spectral feature determination process 200. As is known in the art, there may be a light source that is directed onto the sample in order to excite the desired type scattering that is detected by the detector 420. The computer 410 operates on computer software that performs the computations associated with the feature-based identification algorithm 300 depicted in FIGS. 4 and 5.

The spectroscopic techniques described herein may be used in any source-separation process for any type of data, including multispectral and hyperspectral imagery for military and non-military applications.

The system and methods described herein may be embodied in other specific forms without departing from the spirit or essential characteristics thereof. The foregoing embodiments are therefore to be considered in all respects illustrative and not meant to be limiting.

What is claimed is:

1. A method comprising:
   for at least one source, identifying primary spectral features of source spectroscopic data obtained for at least one source;
   storing data describing the primary spectral features of the at least one source;
   first analyzing sample spectroscopic data obtained for a sample with respect to said data describing the primary spectral features of the at least one source to determine whether the sample spectroscopic data contains the primary spectral features for the at least one source;
   generating a reduced relevant library spectra by eliminating from further consideration a source whose primary spectral features are determined not be present in the sample spectroscopic data; and
   second analyzing said sample spectroscopic data with respect to the reduced relevant library spectra in order to identify one or more sources present in the sample.

2. The method of claim 1, wherein said identifying comprises analyzing the source spectroscopic data for the at least one source to determine one or more spectral features that are a subset of said source spectroscopic data.

3. The method of claim 1, wherein said identifying comprises identifying primary spectral features of source spectroscopic data for the at least one source that is a substance of interest whose presence is desired to be determined in the sample spectroscopic data, and said second analyzing comprises analyzing the sample spectroscopic data to identify one or more substances of interest that are present in the sample.

4. The method of claim 1, wherein said identifying comprises identifying primary spectral features of the at least one source that is an object of interest whose presence is desired to be determined in the sample spectroscopic data that represents an image of a scene, and said second analyzing comprises analyzing the sample spectroscopic data to identify one or more objects of interest that are present in the image.

5. A method comprising:
   for each of a plurality of substances, identifying primary spectral features in spectroscopic data for each the plurality of substances;
   storing data describing the primary spectral features for each of the plurality of substances;
   first analyzing sample spectroscopic data obtained for a sample with respect to said data describing the primary spectral features of each of the plurality of substances to determine whether the sample spectroscopic data contains the primary spectral features for any of the plurality of substances;
   generating a reduced relevant library spectra by eliminating from further consideration one or more substances whose primary spectral features are determined not to be present in the sample spectroscopic data; and
   second analyzing said sample spectroscopic data with respect to the reduced relevant library spectra in order to identify one or more substances present in the sample based on said sample spectroscopic data.

6. The method of claim 5, wherein said identifying comprises analyzing spectroscopic data for each of the substances to determine one or more spectral features for each substance that are a subset of the spectroscopic data for the corresponding substance.

7. A computer readable storage medium encoded with instructions, that when executed by a computer, cause the computer to perform functions that analyze sample spectroscopic data for a sample to separate spectral data for at least one source from the sample spectroscopic data, the functions comprising:

first analyzing the sample spectroscopic data obtained for a sample with respect to data describing primary spectral features for the at least one source to determine whether the sample spectroscopic data contains the primary spectral features for the at least one source;

generating a reduced relevant library spectra by eliminating from further consideration a source whose primary spectral features are determined not to be present in the sample spectroscopic data; and second analyzing said sample spectroscopic data with respect to the reduced relevant library spectra in order to identify one or more sources present in the sample.

8. The computer readable storage medium of claim 7, wherein said instructions for said first analyzing comprise instructions for analyzing the sample spectroscopic data with respect to said data describing the primary spectral features which are a subset of spectroscopic data for the at least one source.

9. The computer readable storage medium of claim 7, wherein said instructions for said second analyzing comprise instructions for analyzing the sample spectroscopic data to identify the at least one source that is a substance of interest in said sample.

10. The computer readable storage medium of claim 7, wherein said instructions for said second analyzing comprise instructions for analyzing the sample spectroscopic data to identify the at least one source that is an object of interest in the sample, wherein the sample spectroscopic data represents an image of a scene.

11. A system for analyzing sample spectroscopic data for a sample to separate spectral data for at least one source from the sample spectroscopic data, comprising:

a spectroscopic detector that is configured to detect scattered energy from a sample and to generate sample spectroscopic data representing said detected scattered energy;

a processor connected to the spectroscopic detector, wherein the processor is configured to:

first analyze the sample spectroscopic data with respect to data describing primary spectral features for the at least one source to determine whether the sample spectroscopic data contains the primary spectral features for the at least one source;

generate a reduced relevant library spectra by eliminating from further consideration a source whose primary spectral features are determined not to be present in the sample spectroscopic data; and second analyze said sample spectroscopic data with respect to the reduced relevant library spectra in order to identify one or more sources present in the sample.

12. The system of claim 11, wherein the processor is configured to first analyze said sample spectroscopic data with respect to data describing the primary spectral features which are a subset of spectroscopic data for the at least one source.

13. The system of claim 11, wherein the processor is configured to perform said second analyzing to identify the at least one source that is a substance of interest in said sample.

14. The system of claim 11, wherein the processor is configured to perform said second analyzing to identify the at least one source that is an object of interest in the sample that represents an image of a scene.

* * * * *

UNITED STATES PATENT AND TRADEMARK OFFICE
CERTIFICATE OF CORRECTION

| | |
|---|---|
| PATENT NO. | : 7,502,693 B1 |
| APPLICATION NO. | : 11/862803 |
| DATED | : March 10, 2009 |
| INVENTOR(S) | : Mohamed-Adel Slamani |

It is certified that error appears in the above-identified patent and that said Letters Patent is hereby corrected as shown below:

Column 1, line 39, replace "This techniques reduces" with -- This technique reduces --;

Column 3, line 15, replace "is repeated from" with -- is repeated for --; and line 46, replace "the identify of" with -- the identity of --.

Signed and Sealed this

Nineteenth Day of May, 2009

JOHN DOLL
*Acting Director of the United States Patent and Trademark Office*